United States Patent
Dempster et al.

(10) Patent No.: US 7,312,451 B2
(45) Date of Patent: Dec. 25, 2007

(54) DETERMINATION OF DOUGH DEVELOPMENT USING NEAR INFRARED RADIATION

(75) Inventors: Richard Dempster, Manhattan, KS (US); Maureen Olewnik, Manhattan, KS (US); Virgil S. Smail, Manhattan, KS (US)

(73) Assignee: American Institute of Baking, Manhattan, KS (US)

( * ) Notice: Subject to any disclaimer, the term of this patent is extended or adjusted under 35 U.S.C. 154(b) by 529 days.

(21) Appl. No.: 10/874,871

(22) Filed: Jun. 22, 2004

(65) Prior Publication Data

US 2005/0129822 A1   Jun. 16, 2005

Related U.S. Application Data

(60) Provisional application No. 60/480,681, filed on Jun. 23, 2003.

(51) Int. Cl.
*G01J 5/02* (2006.01)
(52) U.S. Cl. .................................. 250/339.11
(58) Field of Classification Search .................. None
See application file for complete search history.

(56) References Cited

U.S. PATENT DOCUMENTS

| 6,342,259 B1 | 1/2002 | Wesley et al. | |
| 2002/0137216 A1* | 9/2002 | Chen et al. | 436/20 |
| 2005/0186317 A1* | 8/2005 | Dempster et al. | 426/549 |
| 2006/0172040 A1* | 8/2006 | Tilley et al. | 426/94 |

FOREIGN PATENT DOCUMENTS

WO    WO02054061 A1 *  7/2002

\* cited by examiner

*Primary Examiner*—Dave Porta
*Assistant Examiner*—Casey Bryant
(74) *Attorney, Agent, or Firm*—Tracey Truitt

(57) ABSTRACT

Improved techniques for estimating dough development times are provided in order to permit rapid and accurate forecasts of dough development times in commercial baking operations with different lots of wheat flour. The method of the invention involves directing near infrared radiation against a dough formulation during mixing thereof, and collecting a plurality of time-dependant absorbance spectra; the spectral data are then analyzed, preferably by calculating magnitude ratios at predetermined spectral absorbances, and then estimating the dough development time as a function of the magnitude ratios.

11 Claims, No Drawings

US 7,312,451 B2

DETERMINATION OF DOUGH DEVELOPMENT USING NEAR INFRARED RADIATION

CROSS-REFERENCE TO RELATED APPLICATION

This application claims the benefit of provisional application Ser. No. 60/480,681 filed Jun. 23, 2003. This provisional application is incorporated by reference herein.

BACKGROUND OF THE INVENTION

1. Field of the Invention

The present invention is broadly concerned with methods for estimating dough development times when using specific wheat flours in doughs. More particularly, the invention is concerned with such methods that are particularly suited for the production of commercial bread products, and that permit a commercial baker to pretest lots of wheat flour to determine optimum dough development times when using the respective flours.

2. Description of the Prior Art

The bread baking industry is a high volume, low profit margin (per unit) food manufacturing industry that often relies on subjective determinations made by operators in the dough mixing area. While improvements have been made in dough mixers to standardize mixing operations, decisions with respect to adequacy of dough mixing are based on operator experience, and such decisions often err on the side of conservatism and result in loss of efficiency and/or productivity.

Dough mixing is a physical, chemical, physiocochemical, and biochemical process, and it is an extremely important step in the conversion of flour and other ingredients into an edible bakery product. The mixing process promotes hydration by exposing new surfaces of the flour particles for interaction with water, blends all ingredients into a uniform dough mixture, and results in dough development. This development involves the stretching of long molecules from an unperturbed state to a more extended configuration. The length of the development stage depends on the time required to extend the large molecules and to orientate them in the direction of shear.

Dough characteristics vary based on ingredients, environment, and operation system, and they can be measured by different kinds of instruments through imitative (mixograph, farinograph, and alveograph), empirical (extensigraph), or fundamental (rheometers) means. Additionally, dough development based on change in physical dough consistency can be determined during mixing by recording the torque on mixer blades or the power consumed. While all of these measurements are based on changes in physical properties of a dough, the physical changes are mostly related to chemical interactions that occur during dough mixing. These chemical interactions are of both covalent (disulfide bonds, glucosidic bonds, peptide bonds) and non-covalent (hydrogen bonds, hydrophobic interactions, ionic bonds, and van der Waals bonds) nature. The physical and chemical reactions occurring during dough processing are related to gluten and water properties, which change during mixing due to interactions with each other and with other ingredients that are present. Measurements of dough characteristics based on chemical interactions are more challenging than those based on physical properties.

Analytical near infrared reflectance (NIR) spectroscopy is a useful and cost effective method of food analysis at ingredient, processing, and product stages of production. It has been used for routine inspections in agricultural and food systems for three decades. Advantages of this technique are rapid measurements, simple preparation of samples, and ease of operation. The major sources of near infrared absorption are the overtones and combination bands of fundamental vibrations in the mid-infrared spectrum from 4000-600 $cm^{-1}$. NIR spectroscopy has the potential to probe the molecular and chemical changes that occur during dough development because absorbances in the spectra are a direct manifestation of the principal chemical components of dough-water, protein, starch, and fat. Some bakery applications for which MR has been used include the measurement of sucrose, fat, flour, and water content of biscuit dough and monitoring of the staling process of bread.

To provide uniformly consistent dough, mixer operators' grapple with two major variables—flour absorption and mix time. While proper dough development provides consistency throughout the remainder of the production process, bake absorption maximizes the amount of water that can be held by flour, and this often represents the profit margin realized by the baker. In a recent study, NIR was used to predict the processing and product quality characteristics of wheat flour. Within this study, a major conclusion was the ability of NIR to predict bake absorption in the flour with results equal to those of a trained technician's ability to optimize flour absorption. Earlier NIR investigations found that two specific absorbance wavelengths (1160 nm and 1200 nm) varied with mixer power consumption.

SUMMARY OF THE INVENTION

The present invention provides an improved method for estimating dough development times when using dough formulations incorporating particular wheats. The invention thus permits a commercial baker to run relatively quick and inexpensive testing of individual lots of wheat as received, and to estimate therefrom optimum dough development times for doughs using the respective wheat lots. Broadly speaking, the methods of the invention include the steps of forming a dough by mixing together for a typical dough mixing period dough-forming ingredients including the particular flour under investigation. During such mixing period, near infrared radiation is repeatedly over time directed against the dough surface and reflected radiation is collected to yield corresponding absorbance spectra. Such spectral data are then employed to determine an estimated optimum dough development mixing time.

In more detail, the method of the invention involves an initial determination of the magnitudes of the absorbance spectra at respective first and second absorbances corresponding to reflected radiation wavelengths. Generally, the first absorbances may relate to a starch absorption band, whereas the second absorbance may relate to a strong protein absorption band. Preferably, the first absorbances are in the neighborhood of 1205 nm (e.g., 1205 nm±10 nm), whereas the second absorbances are in the neighborhood of 1455 nm (e.g. 1455 nm±10 nm). Next, ratios are calculated by dividing the magnitude of the second absorbance by the magnitude of the first absorbance for each spectrum. These ratios are then used to estimate the development time for the dough. Preferably, a cumulative sum of the absorbance ratios is calculated, which permits development time estimation as the maximum positive value derived from the cumulative sum calculation. If desired, a graph of mixing time vs. absorbance ratios can be prepared which illustrates the estimated optimum development time.

In a further aspect of the invention, it is sometimes advantageous to delete errant spectrum from the initially collected spectra in order to eliminate outlier spectrum that can skew the results. In one such technique, each spectrum is examined to determine the slope thereof over a first range below about 800 nm and a second range above 800 nm and below 1100 nm. Any spectrum having a positive net slope over the first range and/or a negative net slope over the second range are eliminated. Still more preferably, the first slope range should be from about 400-800 nm (most preferably from about 545-645 nm), while the second slope range should be from about 800-1100 nm (most preferably from about 950-960 nm).

In carrying out the invention, conventional and commercially available NIR spectrometric equipment can be used. Preferably, this equipment should be capable of detecting diffusely reflected radiation from 400-1700 nm. Similarly, no special requirements are needed for the dough mixing equipment, except that such equipment may need to be modified for installation of an NIR probe. The calculations carried out are readily amenable to computerization using standard software. For example, good results have been obtained by coupling the NIR equipment to a standard PC and performing the required calculation using MATLAB software. Of course, the equipment and software is exemplary only, and equivalents can readily be found.

DETAILED DESCRIPTION OF THE PREFERRED EMBODIMENT

The following example sets forth presently preferred equipment and calculations used in carrying out the methods of the invention. It is to be understood, however, that this example is provided by way of illustration only, and nothing therein should be taken as a limitation upon the overall scope of the invention.

EXAMPLE

In this specific example of estimating dough development time, a dough was formed by mixing together for a period of time dough-forming ingredients including a particular wheat flour. Specifically, the wheat flour tested was 1100 grams of King Midas flour, which is commercial spring wheat flour from ConAgra's Omaha facility. The dough was the type utilized to make white pan bread and included of 100% flour, 7% sugar, 2% salt, 3% shortening, 2% yeast, and variable water (baker's percent).

Near infra-red radiation was directed on a sample of the dough such that the radiation interacted with the sample. The radiation was directed through a NIR/VIS spectrometer, specifically a "DA-7000 NIR/VIS" spectrometer manufactured by "PERTEN INSTRUMENTS", coupled with a "LABTRON" mixer system equipped with a "HOBART" mixer having a double helical agitator and a jacketed "MCDUFFEE" bowl. The bottom of the bowl was modified to include a window in its base, which allowed NIR to pass into the interior of the bowl. The NIR/VIS spectrometer was connected to the mixer system via a fiber optic probe positioned beneath the window. The illumination of the probe conveyed the chopped, high-intensity, broadband radiation to the sample. The wavelengths of the broadband illumination are between 360 nm and 2.6 nm and are produced using a Tungsten-Halogen light source, which closely follows a blackbody radiation source (approximately 3200 degrees Centigrade).

The NIR spectrometer and the Labtron mixer required approximately one hour to warm up before the dough was mixed. Noise and baseline tests for the NIR spectrometer were performed in order to verify that the test would be valid. A sample identification name was selected for the data collection, and a baseline spectrum was recorded for each test. Sample identification and water absorption were also recorded in the computer for the Labtron mixer after a reference Labtron curve was chosen.

The dough was formulated by first adding flour to the mixing bowl, followed by all other ingredients except water. Thirty seconds prior to adding water, the NIR/VIS spectrometer began to direct continuous radiation on the sample and detected reflected radiation. Mixing was started after the addition of water and was continued for approximately 20 minutes at a continuous speed. The NIR/VIS spectrometer was stopped at the completion of the mixing time. The total time of mixing varied, depending on type of flour used as some types of flours require longer mixing times to develop.

Referring to FIG. 1, after the NIR was directed at the sample, radiation, which reflected from the sample, was detected by the spectrometer. Specifically, the radiation was dispersed by a stationary diffraction grating as it entered the NIR/VIS spectrometer. The NIR/VIS spectrometer detected the radiation and focused it on a diode array, which converted the signals into a digital format as time-dependent absorbance spectra. The acquisition of spectra was 2.55 samples per second. The digital signals were received by a "DA-7000" NIR system attached to a computing system with the Windows 95 operating system installed, wherein they were manipulated as described below.

Referring to FIG. 2, a cleaning algorithm was applied to the detected absorbance spectra to remove errant spectra, which were not attributed to the dough or to the mixing of the dough. Errant spectra were identified based on slope of the absorbance spectra. Normal reflected spectra have a negative slope over the range 400 nm to 800 nm and a positive slope over the range 800 nm to 1100 nm, as demonstrated in FIG. 4. Errant spectra lack these slope characteristics and were removed. It was found advantageous to utilize a more specific range to eliminate additional errant spectra. Specifically, for each spectrum, the slopes between a first range of 545 to 645 nm and a second range of 950 nm to 960 nm were calculated. If the slope of the first range was positive and/or the slope of the second range was negative, the spectra were considered errant and were discarded.

Referring to FIG. 3, the start point of sample mixing was then determined from the data. The start point was calculated from the detected spectra by determining an increase in absorbance level at a particular wavelength.

Referring to FIGS. 4 and 5, a development curve was then created utilizing an algorithm based on the ratio between each spectrum's absorbance at 1455 nm and at 1205 nm. The ratio of the sample spectrum of FIG. 4 was calculated by dividing the absorbance at the 1455 peak by the absorbance at the 1205 peak, which equals approximately 0.6/0.37, or 1.62.

After determining the ratio for each non-errant absorbance spectrum, the determined ratio for each spectrum was mean centered. Specifically, the mean ratio for the total number of spectra was determined and then subtracted from each spectrum's ratio. For instance, if the mean ratio of the total number of spectra was 1, then the mean centered ratio of the above example of FIG. 4 would be 1.62-1, or 0.62.

Referring to FIG. 5, a final dough development curve was created from the mean centered ratios by plotting the square (or absolute value) of the cumulative sum of each spectrum's mean centered ratio. Thus, each point presented on the curve of FIG. 5 represents the sum of the ratios for all spectra detected prior to and simultaneously with the point. Mean centered ratios having a negative value allow the slope of the curve to be negative to the right of the peak of the curve.

The optimal dough development time occurred at the peak of the development curve. This was equal to the maximum positive value derived from the cumulative sum calculation. In this example, the optimal develop time was approximately 12.5 minutes after the start of mixing. From FIG. 5, it can be seen that it is advantageous to mix the sample dough for roughly twice the estimated optimal development to ensure that a peak is actually reached.

The algorithms, including the cleaning algorithm, determination of absorbance ratios, cumulative sum calculation, and plotting of the development curve were implemented in MATLAB v.12.0 to automate the manipulation and assembly of the data. The MATLAB scripts were as follows (% indicates a comment line):

```
function [cspc,T] = cleanspc(spc)
% cleaning algorithm function
% This function returns the cleaned spc file and the time
% T which is based on 2.55 samples per second.
[r,c] = size(spc);
tspc = spc;
slope = (tspc(:,113) – tspc(:,111))./3;
slope2 = (tspc(:,50) – tspc(:,30))./20;
J = 1;
for I = 1:r
    if (slope(I) > 0.0) && (slope2(I) < 0.0)
        cspc(J,:) = tspc(I,:);
        T(J) = (I/2.55)/60;
        J = J + 1;
    end
end
return;
function [tspc,T] = process_spc(spc)
% This function will process a spc file for dough development.
% Currently this includes cleaning up the spc file for errant
% captures.
%
%
% Index 118 is wavelength 985
% Index 137 is wavelength 1044, a base line
% Index 162 is wavelength 1205
% Index 212 is wavelength 1455
[r,c] = size(spc);      % Added 4/7/03
stpt = findstart(spc);  % Added 4/7/03
spc = spc(stpt:r,:);    % Added 4/7/03
[tspc,T] = cleanspc(spc);
[r,c] = size(tspc);
tspc(:,c+2) = tspc(:,162)./tspc(:,137);
tspc(:,c+3) = tspc(:,212)./tspc(:,137);
%tspc(:,c+4) = tspc(:,c+3)./(tspc(:,c+2)./tspc(:,c+1));
tspc(:,c+4) = tspc(:,c+3)./tspc(:,c+2);
tspc(:,c+5) = tspc(:,c+4) – mean(tspc(:,c+4));
tspc(:,c+6) = (cumsum(tspc(:,c+5))).^2;
% setup for predicting the end point.
ntspc = tspc(:,c+6)/max(tspc(:,c+6));
done = 0;
I = 1;
while ~done && I < r % Handle run on condition.
    if (T(I) >= 3.0) & (ntspc(I) > 0.1)
        x1 = I;
        done = 1;
    end
    I = I + 1;
end
if I < r
x2 = x1+75;
tspc(2,c+7) = x1;
```

-continued

```
tspc(3,c+7) = x2;
slope1 = (ntspc(x2) – ntspc(x1))/(x2–x1);
x1 = x1 + 75;
x2 = x1 + 75;
slope2 = (ntspc(x2) – ntspc(x1))/(x2–x1);
slope = (slope1+slope2)/2;
b = ntspc(x1) – slope*x1;
tspc(1,c+7) = (((1-b)/slope)/2.5)/60;
disp(tspc(1,c+7));
% Code below is for debugging and can be used
% by removing the %. Currently for testing only.
%if (dt > r) | (dt < 0)
% disp('ERROR');
%else
% disp(T(dt));
% tspc(1,c+7) = T(dt);
%end
end
return;
```

We claim:

1. In a method of estimating dough development time when using a particular wheat flour in the dough, said method including the steps of forming a dough by mixing together for a period of time dough-forming ingredients including said particular flour, directing near infrared radiation against a surface of said dough, and collecting reflected radiation from said dough as a plurality of time-dependant absorbance spectra; the improvement which comprises:

determining the magnitudes of the absorbance spectra within a first neighborhood of 1205 nm and a second neighborhood of 1455 nm;

ascertaining a ratio of the magnitude of the second neighborhood to the magnitude of the first neighborhood for each absorbance spectrum;

calculating a cumulative sum of said ratios;

calculating a maximum positive value from said cumulative sum calculation, and estimating said development time as said maximum positive value derived from said cumulative sum calculation; and basing said development time on the results of said estimating step.

2. The method of claim 1, including the step of deleting any errant spectra from said plurality of absorbance spectra by ascertaining the slopes of each absorbance spectrum over a first range below about 800 nm and a second range above about 800 nm, and deleting any spectra having a positive slope over said first range and/or a negative slope over said second range.

3. The method of claim 2, said first range being from about 400-800 nm, and said second range being from about 800-1100 nm.

4. The method of claim 3, said first range being from about 545-645 nm, and said second range being from about 950-960 nm.

5. The method of claim 1, said first neighborhood being 1205 nm±10 nm, and said second neighborhood being 1455 nm±10 nm.

6. The method of claim 1, including the step of preparing a graph of time vs. said cumulative sum of said ratios, and estimating said dough development time as the positive peak of said graph.

7. In a method of estimating dough development time when using a particular wheat flour in the dough, said method including the steps of forming a dough by mixing together for a period of time dough-forming ingredients including said particular flour, directing near infrared radiation against a surface of said dough, and collecting reflected radiation from said dough as a plurality of time-dependant absorbance spectra, the improvement which comprises:

determining the magnitudes of the absorbance spectra at respective first and second absorbances;

ascertaining a ratio of the magnitude of the second absorbance to the magnitude of the first absorbance for each absorbance spectrum;

estimating said development time as a function of said ratios: and basing said development time on the result of said estimating step.

8. The method of claim 7, said first absorbance being about 1205 nm, and said second absorbance being about 1455 nm.

9. The method of claim 7, including the step of deleting any errant spectrum from said plurality of absorbance spectra by ascertaining the slopes of each absorbance spectrum over a first range below about 800 nm and a second range above about 800 nm, and deleting any spectrum having a positive slope over said first range and/or a negative slope over said second range.

10. The method of claim 9, said first range being from about 400-800 um, and said second range being from about 800-1100 nm.

11. The method of claim 10, said first range being from about 545-645 nm, and said second range being from about 950-960 nm.

\* \* \* \* \*